United States Patent
Herget et al.

(10) Patent No.: US 9,702,847 B2
(45) Date of Patent: Jul. 11, 2017

(54) SYSTEMS AND METHODS FOR DETECTING A SUBSTANCE IN BODILY FLUID

(71) Applicant: Avails Medical, Inc., Palo Alto, CA (US)

(72) Inventors: Meike Herget, Woodside, CA (US); Oren S. Knopfmacher, Palo Alto, CA (US)

(73) Assignee: Avails Medical, Inc., Menlo Park, CA (US)

( * ) Notice: Subject to any disclaimer, the term of this patent is extended or adjusted under 35 U.S.C. 154(b) by 0 days.

(21) Appl. No.: 14/586,802

(22) Filed: Dec. 30, 2014

(65) Prior Publication Data
US 2016/0187334 A1 Jun. 30, 2016

(51) Int. Cl.
| | |
|---|---|
| *G01N 27/414* | (2006.01) |
| *G01N 33/53* | (2006.01) |
| *G01N 33/543* | (2006.01) |
| *G01N 27/60* | (2006.01) |

(52) U.S. Cl.
CPC ......... *G01N 27/4145* (2013.01); *G01N 27/60* (2013.01); *G01N 33/54353* (2013.01); *G01N 33/54373* (2013.01); *G01N 33/54386* (2013.01)

(58) Field of Classification Search
CPC ......... G01N 27/4145; G01N 33/54386; G01N 33/54353
See application file for complete search history.

(56) References Cited

U.S. PATENT DOCUMENTS

| | | |
|---|---|---|
| 4,236,893 A | 12/1980 | Rice |
| 4,314,821 A | 2/1982 | Rice |
| 4,735,906 A | 4/1988 | Bastiaans |
| 4,767,719 A | 8/1988 | Finlan |
| 4,789,804 A | 12/1988 | Karube et al. |
| 4,822,566 A | 4/1989 | Newman |
| 4,977,247 A | 12/1990 | Fahnestock et al. |
| 5,077,210 A | 12/1991 | Eigler et al. |

(Continued)

FOREIGN PATENT DOCUMENTS

| | | |
|---|---|---|
| WO | WO 03/044530 | 5/2003 |
| WO | WO 2012/078340 | 6/2012 |

(Continued)

OTHER PUBLICATIONS

Salm, Eric et al., "Electrical Detection of Nucleic Acid Amplification Using an On-Chip Quasi-Reference Electrode and a PVC REFET," dx.doi.org/10.1021/ac500897t, *Anal. Chem.*, 2014, 86: 6968-6975.

(Continued)

*Primary Examiner* — Paul Hyun
(74) *Attorney, Agent, or Firm* — Levine Bagade Han LLP

(57) ABSTRACT

Various devices, systems and methods for determining a parameter of and/or detecting chemical and biological substances in bodily fluid are described herein. A device or system may include a substrate. An active sensor having an electrical characteristic and/or a control sensor may be disposed on the substrate. In certain variations, a differential between a first signal from the active sensor, and a second signal from the control sensor may be used to determine a parameter of the chemical or biological substance in the sample of bodily fluid.

20 Claims, 11 Drawing Sheets

(56) References Cited

U.S. PATENT DOCUMENTS

| | | | |
|---|---|---|---|
| 5,111,221 | A | 5/1992 | Fare et al. |
| 5,182,005 | A | 1/1993 | Schwiegk et al. |
| 5,447,845 | A | 9/1995 | Chu et al. |
| 5,821,399 | A | 10/1998 | Zelin |
| 5,922,537 | A | 7/1999 | Ewart et al. |
| 6,280,586 | B1 | 8/2001 | Wolf et al. |
| 6,368,795 | B1 | 4/2002 | Hefti |
| 6,391,558 | B1* | 5/2002 | Henkens et al. ............ 435/6.11 |
| 6,548,263 | B1* | 4/2003 | Kapur et al. ................... 506/32 |
| 6,548,311 | B1 | 4/2003 | Knoll |
| 6,780,307 | B2 | 8/2004 | Kidwell |
| 8,508,100 | B2 | 8/2013 | Lee et al. |
| 9,377,456 | B1 | 6/2016 | Herget et al. |
| 2002/0127623 | A1 | 9/2002 | Minshull et al. |
| 2003/0109056 | A1 | 6/2003 | Vossmeyer et al. |
| 2003/0119208 | A1 | 6/2003 | Yoon et al. |
| 2006/0102935 | A1 | 5/2006 | Yitzchaik et al. |
| 2006/0197118 | A1 | 9/2006 | Migliorato et al. |
| 2006/0246426 | A1 | 11/2006 | Woodbury et al. |
| 2006/0286548 | A1* | 12/2006 | Liposky ............. G01N 33/6842 435/5 |
| 2009/0008247 | A1* | 1/2009 | Chen et al. ............. 204/403.14 |
| 2009/0273354 | A1 | 11/2009 | Dhirani et al. |
| 2010/0025660 | A1 | 2/2010 | Jain et al. |
| 2012/0032235 | A1 | 2/2012 | Bikumandla |
| 2012/0077692 | A1 | 3/2012 | Hassibi et al. |
| 2012/0088682 | A1* | 4/2012 | Rothberg ............ C12Q 1/6825 506/9 |
| 2012/0153262 | A1* | 6/2012 | Paranjape et al. ............. 257/24 |
| 2012/0168306 | A1 | 7/2012 | Hassibi et al. |
| 2012/0208291 | A1* | 8/2012 | Davis ................... G01N 33/557 436/501 |
| 2012/0279859 | A1 | 11/2012 | Rothberg et al. |
| 2013/0096013 | A1 | 4/2013 | Esfandyarpour et al. |
| 2014/0057339 | A1 | 2/2014 | Esfandyarpour et al. |
| 2014/0191294 | A1 | 7/2014 | Bikumandla et al. |
| 2014/0349005 | A1 | 11/2014 | Everett et al. |
| 2015/0355129 | A1 | 12/2015 | Knopfmacher |
| 2016/0187332 | A1 | 6/2016 | Herget et al. |
| 2016/0209356 | A1 | 7/2016 | Herget et al. |
| 2016/0266102 | A1 | 9/2016 | Knopfmacher |

FOREIGN PATENT DOCUMENTS

| | | |
|---|---|---|
| WO | WO 2013/096404 | 6/2013 |
| WO | WO 2015/077632 | 5/2015 |
| WO | WO 2015/188002 | 12/2015 |
| WO | WO 2016/109569 | 7/2016 |

OTHER PUBLICATIONS

Estrela, Pedro et al., "Label-Free Sub-picomolar Protein Detection with Field-Effect Transistors," Analytical Chemistry, vol. 82, No. 9, May 1, 2010, 3531-3536.

Hammock, Mallory L. et al., "Electronic readout ELISA with organic field-effect transistors as a prognostic test for preeclampsia," Advanced Materials, 26; 6138-6144, doi: 10.1002/adma.201401829.

Dortet, Laurent et al., "Bloodstream Infections Caused by *Pseudomonas* spp.: How to Detect Carbapenemase Producers Directly from Blood Cultures", Journal of Clinical Microbiology, 52(4):1269-1273, Apr. 2014.

Dortet, Laurent et al., "CarbAcineto NP Test for Rapid Detection of Carbapenemase-Producing *Acinetobacter* spp.", Journal of Clinical Microbiology, 52(7):2359-2364, Jul. 2014.

Dortet, Laurent et al., "Evaluation of the RAPIDECw CARBA NP, the Rapid CARB Screenw and the Carba NP test for biochemical detection of carbapenemase-producing Enterobacteriaceae", J Antimicrob Chemother, 70:3014-3022, 2015.

Dortet, Laurent et al., "Further Proofs of Concept for the Carba NP Test", Antimicrobial Agents and Chemotherapy, 58(2):1269, Feb. 2014.

Dortet, Laurent et al., "'Rapid Identification of Carbapenemase Types in Enterobacteriaceae and *Pseudomonas* spp. by Using a Biochemical Test", Antimicrobial Agents and Chemotherapy, 56(12):6437-6440, Dec. 2012.

Kumar et al.; "Sensitivity Enhancement Mechanisms in Textured Dielectric Based Electrolyte-Insulator-Semiconductor (EIS) Sensors," ECS Journal of Solid State Science and Technology, 4(3):N18-N23 (2015).

Nordmann, Patrice et al., "Strategies for identification of carbapenemase-producing Enterobacteriaceae", J Antimicrob Chemother, 68:487-489, 2013.

Poghossian et al., "Penicillin Detection by Means of Field-Effect Based Sensors: EnFET, Capacitive EIS Sensor or LAPS?", Sensors and Actuators B, 78:237 (2001).

Poirel, Laurent et ai., "Rapidec Carba NP Test for Rapid Detection of Carbapenemase Producers", Journal of Clinical Microbiology, 53(9):3003-3008, Sep. 2015.

Schoning, Michael J., "Playing Around with Field-Effect Sensors on the Basis of EIS Structures, LAPS and ISFETs," Sensors, 5:126-138 (2005).

\* cited by examiner a. Glutamate (Glu) synthesis:

| Reactants | Products | Enzymes |
|---|---|---|
| Glutamine + $H_2O$ | → Glu + $NH_3$ | GLS, GLS2 |
| NAcGlu + $H_2O$ | → Glu + Acetate | N-acetyl-glutamate synthase |
| α-ketoglutarate + NADPH + $NH_4^+$ | → Glu + $NADP^+$ + $H_2O$ | GLUD1, GLUD2[8] |
| α-ketoglutarate + α-amino acid | → Glu + α-keto acid | transaminase |
| 1-Pyrroline-5-carboxylate + $NAD^+$ + $H_2O$ | → Glu + NADH | ALDH4A1 |
| N-formimino-L-glutamate + $FH_4$ | → Glu + 5-formimino-$FH_4$ | FTCD |
| NAAG | → Glu + NAA | GCPII | b. Aspartate synthesis

Asparagine + $H_2O$ → Asparagine acid    Enzyme: asparaginase c. Gluconic acid formation D - (+) - Glucose + $O_2$ $\xrightarrow{GO_x}$ Gluconic Acid + $H_2O_2$

FIG. 7

SYSTEMS AND METHODS FOR DETECTING A SUBSTANCE IN BODILY FLUID

FIELD OF THE INVENTION

The present systems and methods relate generally to devices, systems and methods for detecting various parameters of a chemical or biological substance in bodily fluid.

BACKGROUND

Integration of biosensors on a small scale for e.g., in-home testing is increasingly being favored by healthcare providers, however it has been a challenge for years. Optical-based biosensors require bulky detection equipment and access to power supplies. Vibration sensitive biosensors (AFM, crystal-quartz balance etc.) cannot be built into a hand-held or portable device since background vibration will interfere with the signal. Biosensors made from electrical components have been considered as a good solution, however existing biosensors face several problems including limitations caused by electrostatic screening in complex media. Several methods to circumvent this problem including sample dilution and pulsed electrical properties have been explored, resulting in additional sample processing steps and the dilution of the analyte, or adding complexity to the device design. In addition, reference and calibration processes prior to use of the biosensors complicates their use.

Existing biosensors used to detect substances in bodily fluid suffer from a number of other limitations as well. For example, existing biosensors may be utilized for analyte detection; however, due to the inability to control various environmental factors surrounding the sample of bodily fluid and the biosensor, signals associated with this detection are often not accurate, not reproducible and do not provide a reliable or stable readout. Examples of existing biosensors can be found in Pedro Estrela et al., *Label-Free Sub-picomolar Protein Detection with Field-Effect Transistors*, Anal. Chem. 2010, 82, 3531-3536 and Eric Salm et al., *Electrical Detection of Nucleic Acid Amplification Using an On-ChipQuasi-Reference Electrode and a PVC REFET*, Anal. Chem. 2014, 86, 6968-6975, each of which is herein incorporated by reference.

As a result of the above limitations and restrictions, there is a need for an improved device, system and method for detecting chemical and biological substances in bodily fluid that minimizes or eliminates such limitations and restrictions.

BRIEF SUMMARY

Various electrical devices, systems and methods for determining a parameter of and/or detecting a chemical and biological substances in bodily fluid are described herein.

In one example, such a device includes a substrate having an active sensor; wherein the active sensor comprises a first electrical component having an electrical characteristic; a functionalized structure comprising a plurality of binding receptors each having at least one functional group associated therewith such that the functional group on each of the binding receptors permits securing each of the binding receptors to a first layer of the sensor in a uniform manner, wherein the binding receptor is configured to interact with the substance such that interaction of the substance with the functionalized structure results in a change in the electrical characteristic of the first electrical component; and wherein the first electrical component is configured to generate a first signal upon the application of an electrical stimulus, the first signal being indicative of the changed electrical characteristic of the first electrical component and where the changed electrical characteristic allows determining the parameter of the substance.

A variation of the device can include a configuration where a distance between a binding site of the functionalized structure and the active sensor is minimized by the lack of an adhesion layer.

In such devices, the electrical stimulus can include altering an electrical parameter selected from the group comprising: frequency, current, voltage, resistance, impedance, capacitance, conductivity, induction, threshold voltage, transconductance, subthreshold swing, piezo-resistivity, magnetic field, and electrical noise.

The binding receptor of the devices described herein can include a protein selected from the group consisting of an engineered protein and an engineered scaffold protein.

In an additional variation, devices under the present disclosure can further include a second electrical component having an electrical characteristic, wherein interaction of the substance with the active sensor or the control sensor does not result in a change in the electrical characteristic of the second electrical component.

The improved binding receptors described herein can include a functional group that is directly engineered onto the binding receptor.

Variations of the device include the functionalized structure being positioned on the substrate or active sensor or in a location separate from the substrate, wherein the functionalized structure is configured to bind the substance, wherein binding of the substance with the functionalized structure produces or results in the release of one or more ions which are detected by the first electrical component or cause a change in the electrical characteristic of the first electrical component.

In an additional variation, the functionalized structure can be positioned on the substrate or active sensor or in a location separate from the substrate, wherein the functionalized structure is configured to bind the substance, wherein binding of the substance with the functionalized structure changes the electrical characteristic of the first electrical component.

The substrate can be positioned in a first location and the functionalized structure can be positioned in a second location separate from the substrate, wherein the functionalized structure is configured to bind to the substance, wherein after binding the substance undergoes a reaction which changes the electrical characteristic of the first electrical component of the active sensor.

The substances screened in the present devices can include a therapeutic, drug, biological moiety, chemical moiety, protein, toxin, ion, antibody, peptide, oligonucleotide, pathogen (e.g., bacteria, viruses, fungi), cells (tumor cells, blood cells, other bodily cells), or ligands.

The high-k dielectric layer described herein can include, but is not limited to, aluminum oxide, titanium oxide, zirconium oxide, yttrium oxide, silicon oxide, tantalum oxide, hafnium oxide and silicon nitride. The immobilization structure can further include nanoparticles and/or a metal layer for adhering to the layer.

In addition, the devices described herein can comprise a disposable structure, wherein a plurality of active and control sensors are positioned on the disposable structure.

In an additional variation, devices for determining a parameter of a substance in a test substance can include a substrate; a first electrical component having an electrical characteristic, the first electrical component comprising an active sensor having a covering layer; a functionalized structure comprising a binding receptor free from endogenous functional groups and having a targeted functional group, where the targeted functional group immobilizes the binding receptor to the covering layer such that the binding receptor extends no more than 5 nm from the covering layer to minimize a screening length of the functionalized structure, where the binding receptor is configured to interact with the test substance such that interaction of the test substance with the functionalized structure alters the electrical characteristic of the first electrical component; and wherein application of an electrical stimulus to the first electrical component generates a first signal from the first electrical component being indicative of the changed electrical characteristic of the first electrical component. In additional variations of the device, the binding receptor can extend beyond 5 nm as needed while still providing an acceptable screening length for the desired application.

The present disclosure also includes methods for determining a parameter of a substance in a test sample. In one variation, such a method includes providing a substrate having an active sensor covered in a first layer and having a first electrical component, wherein the active sensor comprises at least one functionalized structure in electrical communication with the active sensor and wherein the control sensor comprises a second electrical component having an electrical characteristic, where the functionalized structure includes a binding receptor having a functional group coupled thereto such that the functional group secures the binding receptor to the functionalized structure without the need of an adhesion layer to minimize a distance between a surface of the functionalized structure and the active sensor; binding the substance to the functionalized structure, wherein after binding, the functionalized structure affects the first electrical component to produce a changed electrical characteristic, where the changed electrical characteristic varies from the electrical characteristic; determining a comparison between the electrical characteristic and the changed electrical characteristic; using the comparison to determine at least one parameter of substance in the test sample; and producing an output of the at least one parameter.

In an additional variation, the method can include a functionalized structure that is positioned on the substrate or active sensor or in a location separate from the substrate, wherein the functionalized structure binds the substance, wherein binding of the substance with the functionalized structure produces or results in the release of one or more ions which are detected by the first electrical component or cause a change in the electrical characteristic of the first electrical component.

BRIEF DESCRIPTION OF THE SEVERAL VIEWS OF THE DRAWINGS

FIG. 7 illustrates various reactions that a bound chemical or biological substance may undergo.

DETAILED DESCRIPTION

Figure 1:
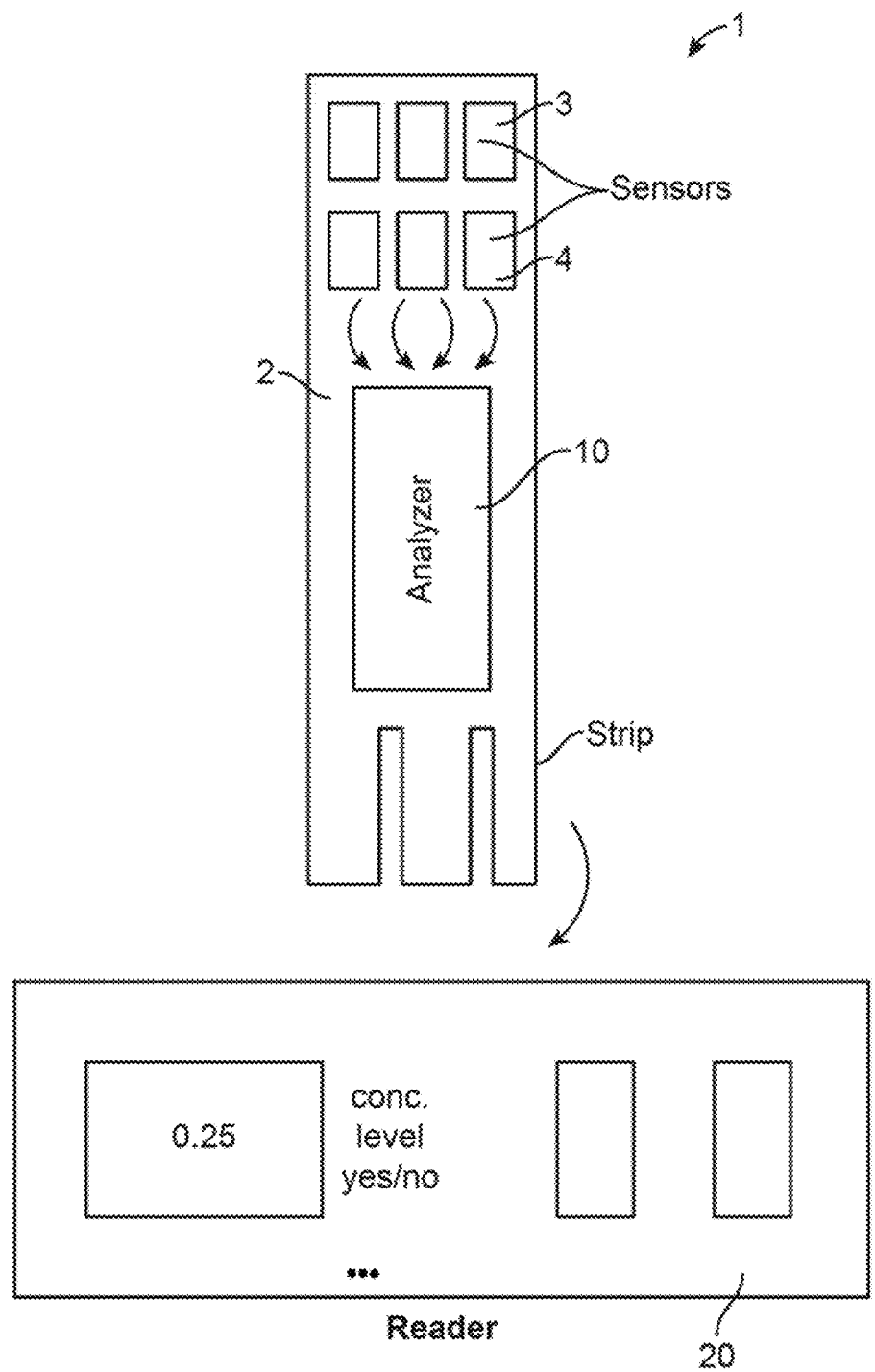
FIG. 1 illustrates a variation of a system for detecting a chemical or biological substance in bodily fluid including a substrate having active and control sensors and an analyzer, and a reader.

Variations of the devices are best understood from the detailed description when read in conjunction with the accompanying drawings. It is emphasized that, according to common practice, the various features of the drawings may not be to-scale. On the contrary, the dimensions of the various features may be arbitrarily expanded or reduced for clarity and not all features may be visible or labeled in every drawing. The drawings are taken for illustrative purposes only and are not intended to define or limit the scope of the claims to that which is shown.

In certain variations, a device, e.g., an electrical device or biosensor, for determining a parameter of and/or for detecting a chemical or biological substance in bodily fluid is provided. The device includes a substrate. One or more active sensors and one or more control sensors may be disposed on the substrate.

The active sensor includes one or more first electrical components having an electrical characteristic or property. One or more functionalized structures are disposed on, near or in a vicinity of the substrate or active sensor. The functionalized structure is configured to interact with, e.g., couple with or bind, the chemical or biological substance, e.g., one or more moieties of the chemical or biological substance. The interaction of the chemical or biological substance with the functionalized structure results in a change in the electrical characteristic or property of the electrical component of the active sensor.

The control sensor comprises one or more second electrical components having an electrical characteristic. However, the control sensor is configured such that interaction of the chemical or biological substance with the active sensor and/or the control sensor does not result in a change in the electrical characteristic of the second electrical components of the control sensor.

The first electrical component of the active sensor produces a signal, where the signal is indicative of the change in the electrical characteristic of the first electrical component caused by the interaction of the functionalized group with the chemical or biological substance in the bodily fluid. For example, the signal may be indicative of a changed current, voltage, capacitance or other electrical characteristic. The interaction between the functionalized group and the chemical or biological substance may take place on the active sensor or off the active sensor or substrate in a separate location. Simultaneously, the second electrical component of the control sensor produces a control signal. The differential between the signal from the first electrical component of the active sensor, and the signal from the second electrical component of the control sensor is used to determine the parameter of the chemical or biological substance in the sample of bodily fluid. Indeed, the device, via the simultaneous use and detection of a control sensor, provides a self-calibration.

The differential signal may be used to determine a variety of parameters or characteristics of the chemical or biological substance, or to detect the presence of the chemical or biological substance. In certain variations, the differential signal may be used to determine the concentration of the chemical or active substance. The differential signal may be used to determine the concentration of a variety of ions present in the chemical or biological substance or in the sample of bodily fluid. For example, the differential signal may be used to determine the pH of the chemical or biological substance.

In certain variations, the differential between the signal produced by the active sensor and the signal produced by the control sensor is indicative of, corresponds to, or is used to determine the concentration of the chemical or biological substance in the sample of bodily fluid. Indeed, the control sensor signal may correspond to a known concentration, such that the differential between the control signal and the signal from the active sensor may be used to deduce or determine the concentration of the chemical or biological substance in the sample of bodily fluid.

The comparison between the signal of the active sensor and the signal of the control sensor may be the differential change ($\Delta S$) in an electrical characteristic, e.g., current, voltage, capacitance, resistance or threshold voltage, of the active sensor (S1) vs the control sensor (S2), where the comparison yields a differential signal is ($\Delta S = S1 - S2$).

In other variations, the signal produced by the active sensor, which is indicative of the changed electrical characteristic or the change in the electrical characteristic of the first electrical component which change occurs as a result of the interaction of the functionalized group with the chemical or biological substance, may be indicative of a changed current, voltage, capacitance or other electrical characteristic. For example, the signal or detected current may correspond to a known concentration, such that the concentration can be deduced from the detected current, or current change, or the concentration may be deduced from a detected change in another electrical characteristic or property which corresponds to a known concentration.

The functionalized structure is configured to interact with the chemical or biological substance of the sample of bodily fluid. As described supra, the interaction of the chemical or biological substance with the functionalized structure may result in a change in the electrical characteristic or property of the electrical component of the active sensor.

In any of the variations described herein, the electrical components may include a transistor, a capacitor, a resistor or an inverter or any other suitable electrical component known to persons have ordinary skill in the art.

A variety of interactions between the chemical or biological substance and the functionalized structure and/or related reactions are contemplated, where such interactions and/or reactions result in a change, or cause a change, in the electrical characteristic or property of the electrical component of the active sensor.

In one variation, one or more functionalized structures are disposed on the active sensor and are configured to bind to the chemical or biological substance. The binding of the chemical or biological substance by the functionalized structure results in a change in an electrical characteristic of the electrical component of the active sensor. For example, the binding of a charged moiety or ion of a chemical or biological substance by a functionalized structure may result in an increase or decrease in charge density on or in a vicinity of the active sensor or a change in current.

In another variation, one or more functionalized structures are disposed on the substrate or the active sensor, and are configured to bind to the chemical or biological substance. The binding of the chemical or biological substance by the functionalized structure produces one or more ions which diffuse to the surface of the active sensor and cause a change in an electrical characteristic of the electrical component of the active sensor. For example, the produced ions may come into contact with, bind or otherwise interact with the active sensor, e.g., causing an increase or decrease in charge density of the active sensor or a change in current. Optionally, the functionalized structures may be disposed in another location, separate from the substrate. The produced ions may then flow over the surface of the active sensor, and interact with the active sensor, causing a change in the electrical characteristic of the electrical component of the active sensor.

In another variation, one or more functionalized structures are disposed on the substrate or the active sensor, and are configured to bind to the chemical or biological substance. The bound chemical or biological substance undergoes a reaction with one or more reagents, thereby producing one or more ions which diffuse to the surface of the active sensor and cause a change in an electrical characteristic of the electrical component of the active sensor. For example, the produced ions may come into contact with, bind or otherwise interact with the active sensor, e.g., causing an increase or decrease in charge density of the active sensor or a change in current. Optionally, the functionalized structures may be disposed in another location, separate from the substrate. Where the reaction takes place in a location which is separated from the substrate, the produced ions may flow to and over the surface of the active sensor, and interact with the active sensor, causing a change in the electrical characteristic of the electrical component of the active sensor.

In another variation, the one or more functionalized structures may be in the form of a permeable membrane or other filter, which is disposed on the active sensor. The membrane or filter is configured to allow for the passage of the target chemical or biological substance or a produced ion, such that the substance or ion may interact with the active sensor, while the membrane or filter blocks or restricts the passage of other moieties or ions, e.g., based on size or other property. The ions may be produced as a result of the binding of the chemical or biological substance by the functionalized structure or as a result of a reaction between a bound substance and a reagent. The ions may diffuse or flow, from a local or remote location, over the surface of the active sensor, after passing through a membrane of filter, and cause a change in an electrical characteristic of the electrical component of the active sensor. For example, the produced ions may come into contact with, bind or otherwise interact with the active sensor, e.g., causing an increase or decrease in charge density of the active sensor or a change in current. Optionally, the membrane, filter or other functionalized structure may capture the target substance or ions, but allow the passage of other non-target ions. Optionally, a membrane, filter or other functionalized structure may block background charge, where a charge or lack of charge may be detected when a particle flows through a membrane and past the sensor.

In certain variations, a device, e.g., an electrical device or a biosensor, for determining a parameter of and/or for detecting a chemical or biological substance in bodily fluid is provided. The device includes a substrate. One or more active sensors may be disposed on the substrate.

The active sensor includes one or more first electrical components having an electrical characteristic or property. One or more functionalized structures are disposed on, near or in a vicinity of the substrate or active sensor. The functionalized structure is configured to interact with, e.g., couple with or bind, the chemical or biological substance, e.g., one or more moieties of the chemical or biological substance. The bound chemical or biological substance undergoes a reaction thereby producing a product. The product interacts with the first electrical component which results in a change in the electrical characteristic of the first electrical component. A signal from the first electrical component, the signal being indicative of the changed electrical characteristic or the change in the electrical characteristic, may be used to determine the parameter of the chemical or biological substance in the sample of bodily fluid.

The signal from the first electrical component of the active sensor may be used to determine a variety of parameters or characteristics of the chemical or biological substance, or to detect the presence of the chemical or biological substance. In certain variations, the signal may be used to determine the concentration of the chemical or active substance. The signal may be used to determine the concentration of a variety of ions present in the chemical or biological substance. For example, the signal may be used to determine the pH of the chemical or biological substance.

In certain variations, the signal produced by the active sensor is indicative of corresponds to, or is used to determine the concentration of the chemical or biological substance in the sample of bodily fluid. Indeed, the signal may correspond to a known concentration, such that the signal from the active sensor may be used to deduce the concentration of the chemical or biological substance in the sample of bodily fluid.

In other variations, the signal produced by the active sensor, which is indicative of the changed electrical characteristic or the change in the electrical characteristic of the first electrical component, may be indicative of a changed current, voltage, capacitance or other electrical characteristic. For example, the signal or detected current may correspond to a known concentration, such that the concentration can be deduced from the detected current.

In any of the variations described herein, the electrical components may include a transistor, a capacitor, a resistor or an inverter or any other suitable electrical component known to persons have ordinary skill in the art.

A variety of interactions between the chemical or biological substance and the functionalized structure and/or related reactions are contemplated, where such interactions and/or reactions result in a change, or cause a change, in the electrical characteristic or property of the electrical component of the active sensor.

In one variation, one or more functionalized structures are disposed on the substrate or the active sensor, and are configured to bind to the chemical or biological substance. The binding of the chemical or biological substance by the functionalized structure produces one or more ions which diffuse to the surface of the active sensor and cause a change in an electrical characteristic of the electrical component of the active sensor. For example, the produced ions may come into contact with, bind or otherwise interact with the active sensor, e.g., causing an increase or decrease in charge density of the active sensor or a change in current. Optionally, the functionalized structures may be disposed in another location, separate from the substrate. The produced ions may then flow over the surface of the active sensor, and interact with the active sensor, causing a change in the electrical characteristic of the electrical component of the active sensor.

In another variation, one or more functionalized structures are disposed on the substrate or the active sensor, and are configured to bind to the chemical or biological substance. The bound chemical or biological substance undergoes a reaction with one or more reagents, thereby producing one or more ions which diffuse to the surface of the active sensor and cause a change in an electrical characteristic of the electrical component of the active sensor. For example, the produced ions may come into contact with, bind or otherwise interact with the active sensor, e.g., causing an increase or decrease in charge density of the active sensor or a change in current. Optionally, the functionalized structures may be disposed in another location, separate from the substrate. Where the reaction takes place in a location which is separated from the substrate, but the produced ions may flow over the surface of the active sensor, and interact with the active sensor, causing a change in the electrical characteristic of the electrical component of the active sensor.

In one variation, the bound chemical or biological substance (on the substrate or in a remote location) may undergo a reaction which produces or results in the release of one or more ions which flow over the active sensor and cause a change in pH or other ion concentration. For example, the change in pH may be detected by the first electrical component of the active sensor, which may have a proton sensitive layer disposed thereon. The change in pH or other ion concentration may cause a change in the electrical characteristic of the first electrical component.

In another variation, the one or more functionalized structures may be in the form of a permeable membrane or other filter, which is disposed on the active sensor. The membrane or filter is configured to allow for the passage of the target chemical or biological substance or a produced ion, such that the substance or ion may interact with the active sensor, while the membrane or filter blocks or restricts the passage of other moieties or ions, e.g., based on size or other property. The ions may be produced as a result of the binding of the chemical or biological substance by the functionalized structure or as a result of a reaction between a bound substance and a reagent. The ions may diffuse or flow, from a local or remote location, over the surface of the active sensor, after passing through a membrane of filter, and cause a change in an electrical characteristic of the electrical component of the active sensor. For example, the produced ions may come into contact with, bind or otherwise interact with the active sensor, e.g., causing an increase or decrease in charge density of the active sensor or a change in current. Optionally, the membrane, filter or other functionalized structure may capture the target substance or ions, but allow the passage of other non-target ions. Optionally, a membrane, filter or other functionalized structure may block background charge, where a charge or lack of charge may be detected when a particle flows through a membrane and past the sensor.

The various reactions described herein may allow indirect detection, where the product of the reaction may diffuse to the surface of the sensor where it interacts with the sensor. This helps circumvent electrostatic screening issues that might otherwise arise.

In certain variations, the substrate may also include a control sensor (as described supra). The control sensor includes a second electrical component having an electrical characteristic. Binding of the chemical or biological substance to the active sensor or the control sensor does not result in a change in the electrical characteristic of the second electrical component of the control sensor.

The active and control sensor are used simultaneously, where both are disposed on the substrate. A differential between a signal from the first electrical component of the active sensor, the signal being indicative of the changed electrical characteristic or the change in the electrical characteristic, and a signal from the second electrical component of the control sensor may be used to determine the parameter of the chemical or biological substance in the sample of bodily fluid, as described supra.

In certain variations, the devices described herein may be part of a sensor or detection system. For example, the device may include, be coupled to, or be in communication with an analyzer. The analyzer may be configured to analyze the signals received from the first and/or second electrical components of the device or biosensor and to determine the differential between the signals. The system may also include a reader, where the reader includes, is coupled to or is in communication with the analyzer. The reader is configured to provide an electrical read-out of the analyzed signals and/or the determined parameter, based on the differential signal.

The analyzer may be used to receive or read the signal from the active and control sensors and to perform smart operations to convert measurements to accurate signal readouts and results for both sensors. The analyzer may include an analog/digital converter and/or a multiplexer. The analyzer may be used to provide a comparison, such as a comparison of signals or other differential readout (See FIG. 2), and/or for amplifying the signals. The analyzer may include one or more source-meters or other electronics to apply a voltage or current, to apply a pulsed signal, to read-out a voltage, to read-out a current, and/or to read out a resistance and/or capacitance change or other electrical characteristic change.

The reader may connect to or be coupled to the device, to the analyzer, and/or to the device having an analyzer incorporated therein. The device may be in the form of a strip having a plurality of sensors as described supra. The reader may receive input from the analyzer, and may be used to visualize the detected and analyzed signals or results from the sensors of the device in a simple and user friendly way. The reader may include one or more source-meters or other electronics to apply a voltage or current, to apply a pulsed signal, to read-out a voltage, to read-out a current, and/or to read out a resistance and/or capacitance change or other electrical characteristic change.

In one variation, a device having one or more sensors and an analyzer, e.g., a device strip having a plurality of sensors as described herein, may be inserted into the reader to provide a user-friendly read-out regarding a parameter, (e.g., concentration) of the chemical or biological substance detected by the sensor. The reader may apply different voltages or currents or other electronic properties to the device strip or analyzer and it may receive or provide an output which may be visualized by a user in a simple and effective manner. Optionally, the reader may have capabilities or be configured to communicate via Bluetooth or Wi-Fi or via other wired or wireless mechanisms or modes of communication to one or more other device. Optionally, a controller may be provided, where the controller is coupled to or in communication with the device, e.g., the sensors, analyzer, and/or a reader, such that the controller may be used to control or program the functionality of the device, including the sensors and/or the analyzer. The controller may be coupled to the analyzer or be integrated in the reader. In certain variation, a controller may be located in the substrate (chip), analyzer or the reader.

In certain variations, methods for determining a parameter of a chemical or biological substance in a sample of bodily fluid include one or more of the following steps. Providing a substrate having an active sensor and a control sensor, wherein the active sensor comprises a first electrical component having an electrical characteristic, wherein at least one functionalized structure is disposed on the substrate or the active sensor or in a location remote or separated from the substrate and active sensor, and wherein the control sensor comprises a second electrical component having an electrical characteristic. Coupling or binding the chemical or biological substance to a functionalized structure, wherein the bound chemical or biological substance undergoes a reaction thereby producing a product. Interacting the product with the first electrical component which results in a change in the electrical characteristic of the first electrical component, while not resulting in a change in the electrical characteristic of the second electrical component. Comparing a first signal and a second signal, where the first signal is from the first electrical component of the active sensor, the first signal being indicative of the changed electrical characteristic or a change in the electrical characteristic, and the second signal being from the second electrical component of the control sensor. Using the differential to determine the parameter of the chemical or biological substance in the sample of bodily fluid. Providing an electronic read-out of the determined parameter, based on the differential.

The functionalized structure may be positioned on the substrate or active sensor or in a location separate from the substrate, wherein the functionalized structure couples or binds the chemical or biological substance. Binding or coupling of the chemical or biological substance with the functionalized structure produces or results in the release of one or more ions which are detected by the first electrical component or cause a change in the electrical characteristic of the first electrical component.

The bound or coupled chemical or biological substance may undergo a reaction with one or more reagents which produces or results in the release of one or more ions which are detected by the first electrical component or cause a change in the electrical characteristic of the first electrical component.

The bound or coupled chemical or biological substance may undergo a reaction which produces or results in the release of one or more ions which cause a change in a pH or other ion concentration, wherein the change in pH other ion concentration is detected by the first electrical component or causes a change in the electrical characteristic of the first electrical component.

The bound chemical or biological substance may undergo a reaction in a first location which produces or results in the release of one or more products or ions which flow to the active sensor on the substrate positioned in a second, separate location, where the products or ions are detected by the first electrical component of the active sensor or cause a change in the electrical characteristic of the first electrical component of the active sensor.

The following documents are incorporated herein by reference in their entirety: Hammock, M. L. et al. Electronic readout ELISA with organic field-effect transistors as a prognostic test for preeclampsia; U.S. Provisional Pat. App. No. 61/907,363; and Mathias, W. et al. Selective Sodium Sensing with Gold-Coated Silicon Nanowire Field-Effect Transistors in a Differential Setup. *ACS Nano* 7, 5978-5983 (2013).

The devices, systems or methods for determining a parameter of and/or for detecting a chemical or biological substance in bodily fluid described herein may be utilized with various bodily fluids to detect various parameters of various substances.

Bodily fluid may include, e.g., blood, urine, saliva, tears, ejaculate, odor or other body fluids. Detected substances can include, e.g., hormones, different pathogens, proteins, antibodies, various drugs or therapeutics or other chemical or biological substances. Detected or determined parameters may include, e.g., pH changes, lactose changes, changing concentration, particles per unit time where a fluid flows over the device for a period of time to detect particles, e.g., particles that are sparse, and other parameters.

The various devices, systems or methods described herein may include one or more of the following features described below.

In certain variations, a plurality of conductors may be coupled to the active sensor and/or a plurality of conductors may be coupled to the control sensor. The conductors may be adapted to be electrically coupled to a reader for obtaining an electrical reading from the electrical components of the active and control sensors.

The chemical or biological substance may include, but not be limited to, a variety of substances, e.g., any substance suitable for detection or monitoring, such as, a therapeutic, drug, biological moiety, chemical moiety, protein, ion or antibody.

A variety of functionalized structures may be utilized, e.g. proteins, peptides, antibodies, or chemical moieties. Any of these functionalized structures may be configured or suitable to bind to a therapeutic, drug, biological moiety, chemical moiety, protein, antibody, or ion in the sample of bodily fluid. In other variations, types of functionalized structures include, but are not limited to, a permeable membrane, hydrogel or other filter, e.g., PVC.

In one variation, a functionalized structure may include a binding receptor immobilized on the surface of the active sensor, and the binding receptor (e.g. antibody, protein, peptide) may be capable of binding to any of the chemical or biological substances described herein.

In certain variations, an immobilization structure may be disposed on or in a vicinity of a substrate or active sensor of a device, and a functionalized structure may be coupled to the immobilization structure. For example, the immobilization structure may include a high-K dielectric layer such as an atomic layer deposition ("ALD") or any other technique can be used to deposit the layer (e.g., such as Growing an oxide layer or nitride etc. on top of the sensor). The high-κ dielectric layer may include, but not be limited to, aluminum oxide, titanium oxide, zirconium oxide, yttrium oxide, silicon oxide, tantalum oxide, hafnium oxide and silicon nitride. Optionally, the immobilization structure may include at least a portion made up of nanoparticles and/or a metal layer for adhering to the layer.

In certain variations, the control sensor may be passivated. For example, the control sensor may include a passivation structure such as a self-assembled monolayer (SAM), metal, or polymer layer. The SAM may include alkane or aromatic thiols, aromatic silanes, or any chemical entity having a terminal group that is covalently attached to a surface, a spacer group having a hydrocarbon, or a head group, e.g., such as, —COOH, —CH3, —SH, —NH2, long chain alkyl of any length or aromatic and —OH. The SAM layer can include a silane where the silanes bearing a long, hydrophobic chain of any length e.g. long alkyl chain of any length, e.g. Octadecyldimethylmethoxysilane.

In any of the variations described herein, the device or substrate may be in the form of a disposable structure. The disposable structure may include a plurality of active and/or control or passivated sensors positioned thereon. In certain variations, the device or strip may include an analyzer and/or a reader incorporated therein.

The device or strip may include a plurality of active sensors and/or control sensors. The signals generated by each sensor, e.g., signals resulting from a change to an electrical characteristic of the active sensors, may be read out. The average of all the determined parameter values based on each sensor, e.g., the concentration of a substance, may then be calculated or deduced.

In any of the various devices, systems or methods described herein, various electrical components or sensors may be utilized. The electrical component or sensor may be any suitable transistor, e.g. an OFET (organic field effect transistor) or FET (field effect transistor). For example, a FET may be of any suitable type, and may include a semiconducting layer doped with a n-type or p-type material. A source or source electrode and a drain or drain electrode may be formed in a spaced-apart position on two sides of the semiconducting layer. The source electrode and drain electrode may be each doped having an opposite polarity to the semiconducting layer. A suitable dielectric layer, such as an oxide layer, may underlie the semiconducting layer and the source and drain. A gate electrode underlies the dielectric layer. In other variations, the gate electrode may be on top of the FET or in its vicinity. A substrate layer made from any suitable material such as plastic or glass serves as a support layer and may underlie the gate electrode. In certain variations, the semiconducting layer may have a surface that is opposite to the surface to which the dielectric layer is adhered.

Any of the readers described herein may include electrical components for receiving, digitizing and analyzing the analog electrical signals received from the sensors or for controlling the sensor. Such electrical components may include a suitable computer processor or central processing unit, which may be electrically coupled to the electrical pickups of the reader that electrically engage the sensors, where such a feature is provided. The reader may further include suitable storage or memory, electrically coupled to the processor, for storing computer data. A suitable display can be included in the reader for displaying desired information. The display can be a touch screen, for additionally serving as an input device or terminal. A transmitter or transceiver can be included in the reader, and electrically coupled therein with a processor, for wirelessly transmitting or receiving information between the reader and a suitable remote device.

The reader, alone or in conjunction with another suitable computing device, can be calibrated to convert the change in electrical characteristic of the electrical component into a concentration level of the targeted drug or other substance. In one variation, a suitable algorithm can be provided in software and stored on a memory of the reader or on a remote device in communication with the reader, or programmed onto a chip provided on the reader, so as to permit a processor of the reader to manipulate or process the plurality of measurements provided by the sensors on the a device or strip and arrive at an immediate numerical concentration of the targeted substance.

Exemplary Variations of Systems for Detecting a Biological or Chemical Substance in Bodily Fluid.

FIG. 1 illustrates a variation of a system 1 for determining a parameter of and/or for detecting a chemical or biological substance in a sample of bodily fluid. The system includes a substrate 2. One or more active sensors 3 and one or more control sensors 4 are disposed on the surface of the substrate 2. For example, FIG. 1 shows three active sensors 3 and three control sensors 4; however, it is contemplated that any suitable number of sensors or sensor pairings may be utilized.

The system 1 also includes an analyzer 10. The analyzer 10 is configured to analyze the signals received from the first electrical components of the active sensor 3 and the second electrical component of the control sensor 4. The system also includes a reader 20. The reader 20 is coupled to or in communication with the sensors 3, 4 and/or analyzer 10. The reader 20 is configured to receive an analyzed signal from the analyzer 10, and to provide an electronic read-out of the analyzed signal, e.g., in a visible, user-friendly mode. Optionally, a controller may be coupled to the analyzer or be integrated in the reader to provide control and/or programming.

The active sensor 3 includes one or more first electrical components having an electrical characteristic or property. One or more functionalized structures (not shown), may be disposed on, near or in a vicinity of the substrate 2 or the active sensor 3. The functionalized structure and functionalized structure arrangement may include any of the functionalized structures described herein, e.g., including the functionalized structures illustrated in FIGS. 3A-6 (discussed below). The functionalized structure may interact with (e.g., couple with or bind) the chemical or biological substance. The interaction of the chemical or biological substance with the functionalized structure, or the interaction of an ion or product released or produced by a reaction involving a bound chemical or biological substance, may result in a change in the electrical characteristic or property of the electrical component of the active sensor 3.

The control sensor 4 includes one or more second electrical components having an electrical characteristic. The control sensor 4 is configured such that interaction of the chemical or biological substance with the active sensor 3 and/or the control sensor 4 does not result in a change in the electrical characteristic of the second electrical components of the control sensor 4. For example, the control sensor 4 may be passivated such that the target chemical or biological substance does not bind to or interact with the control sensor 4.

Figure 2:
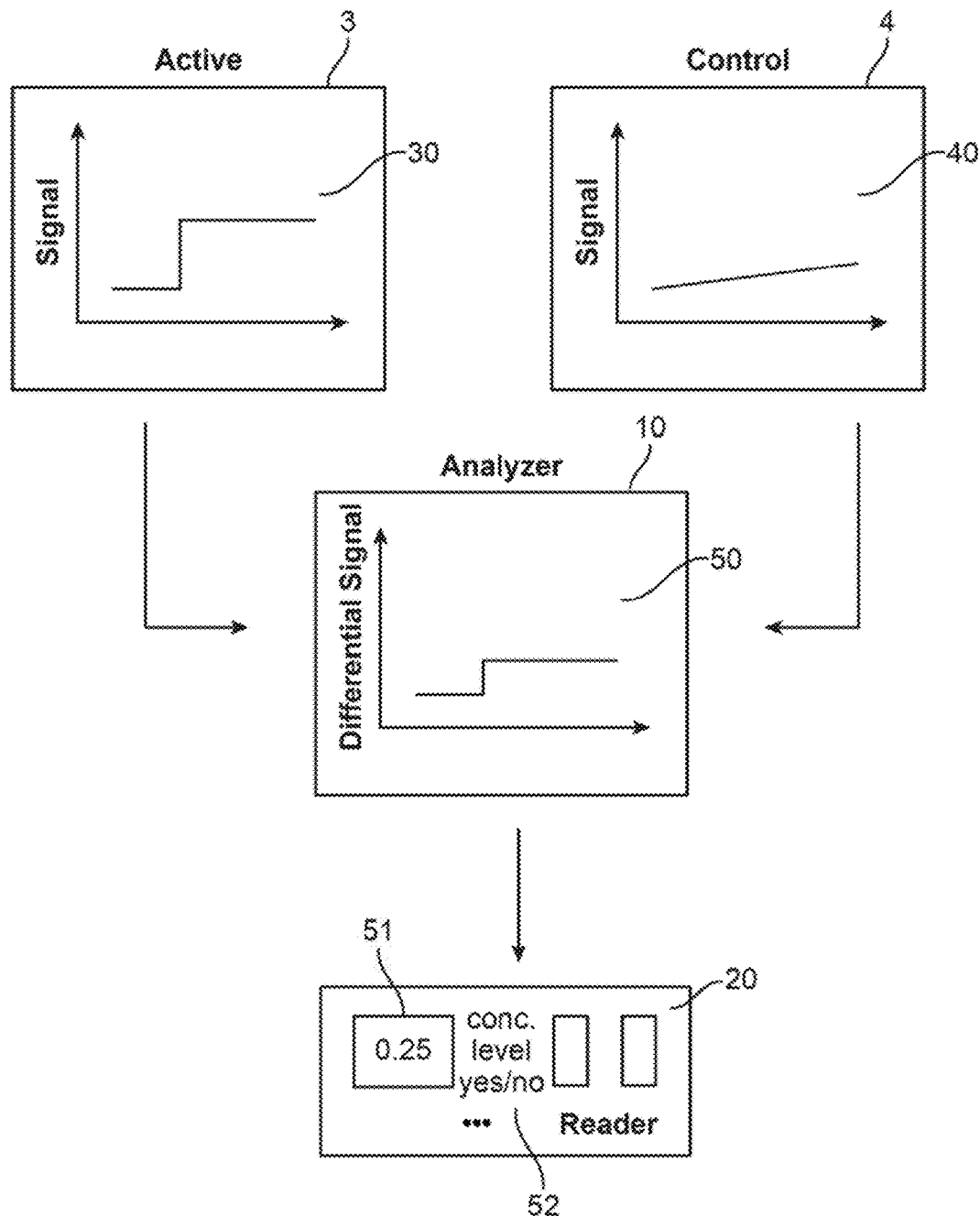
FIG. 2 illustrates a schematic diagram of the signal detection and read out of the system according to FIG. 1.

As illustrated with reference to the schematic in FIG. 2, the first electrical component of the active sensor 3 produces an active signal 30. The active signal 30 is indicative of the changed electrical characteristic or the change in the electrical characteristic of the first electrical component caused by the interaction of the functionalized group or the first electrical component with the chemical or biological substance in the bodily fluid, or a product (e.g., an ion) released from a reaction involving the chemical or biological substance. For example, the active signal 30 may be indicative of a change in current, voltage, capacitance or other electrical characteristic. Simultaneously, the second electrical component of the control sensor 4 produces a control signal 40. The analyzer 10 receives, as input, the active signal 30 from the active sensor 3 and the control signal 40 from the control sensor 4. The analyzer produces a comparison (or a comparison signal) between the signals from the active sensor and the control sensor. For example, such a comparison can include a differential signal 50, being the difference between the active signal 30 and the control signal 40. The analyzer may convert the active and control signals from analog to digital. The differential signal 50 is then transmitted to the reader 20, and used to deduce a parameter, e.g., concentration of the chemical or biological substance in the sample of bodily fluid. The reader 20 than provides a read-out based on the differential signal, in the form of a value 51 of a parameter of the substance, e.g., the concentration of the substance, and/or by indicating whether or not the substance is or is not present 52 in the sample of bodily fluid.

The differential signal 50 may be used to determine a variety of parameters or characteristics of the chemical or biological substance, or to detect the presence of the chemical or biological substance. In certain variations, the differential signal 50 may be used to determine the concentration of various ions present in a target chemical or biological substance or in the sample of bodily fluid. For example, the differential signal 50 may be used to determine the pH of the target chemical or biological substance.

Figure 3A:
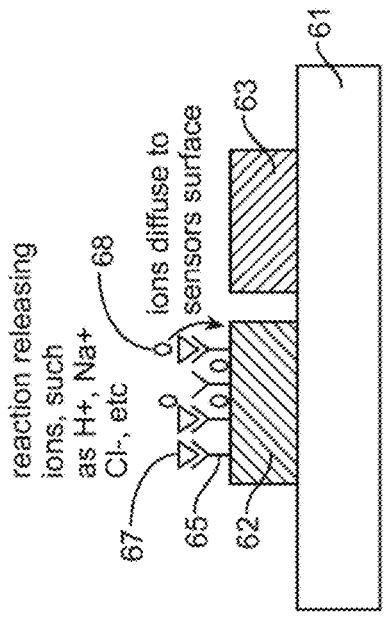
FIG. 3A illustrates a substrate having an active sensor and a control sensor where functionalized structures are disposed on the active sensor.
Figure 3B:
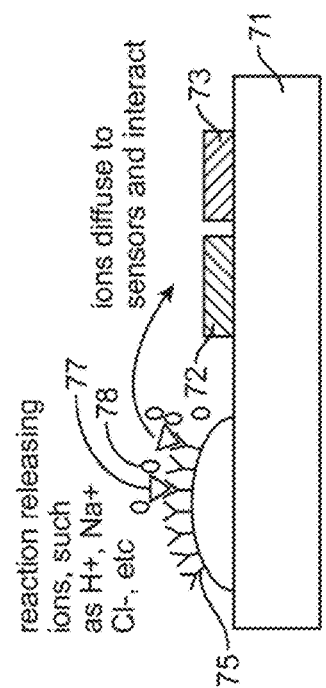
FIG. 3B illustrates a side view of the substrate of FIG. 3A, where a target chemical or biological substance is bound to a functionalized structure and undergoes a reaction which produces ions which diffuse to the surface of the active sensor.

FIGS. 3A-3B illustrate one variation of a device or substrate 61 having one or more functionalized structures 65 disposed thereon. The substrate 61 includes an active sensor 62 and a control sensor 63. Functionalized structures 65 are disposed on the surface of the active sensor 62. As shown in FIG. 3B, a target chemical or biological substance 67 binds to one or more of the functionalized structure 65 and undergoes a reaction which produces one or more ions 68, which diffuse to the surface of the active sensor 62 where they interact with the active sensor 62 and cause a change in an electrical characteristic of the active sensor 62 and/or are detected by the active sensor 62.

Figure 4A:
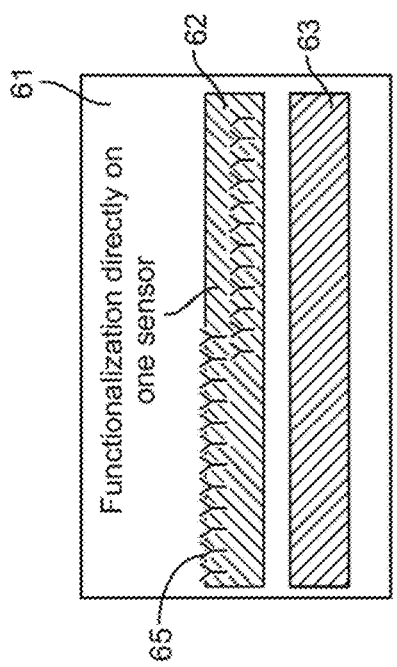
FIG. 4A illustrates a substrate having an active sensor and a control sensor where functionalized structures are disposed on the substrate, adjacent to the active sensor.
Figure 4B:
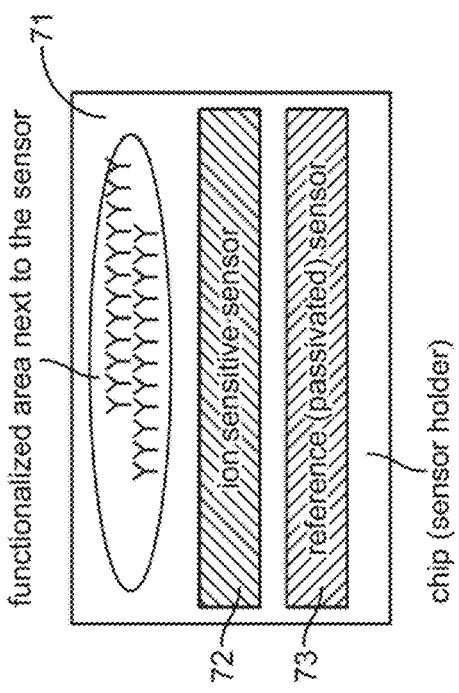
FIG. 4B illustrates a side view of the substrate of FIG. 4A, where a target chemical or biological substance is bound to the functionalized structure and undergoes a reaction which produces ions which diffuse to the surface of the active sensor.

FIGS. 4A-4B illustrate another variation of a device or substrate 71 having one or more functionalized structures 75 disposed thereon. The substrate 71 includes an active sensor 72 and a control sensor 73. Functionalized structures 75 are disposed on the surface of the substrate 71, adjacent to the active sensor 72.

As shown in FIG. 4B, a target chemical or biological substance 77 binds to one or more of the functionalized structure 75 and undergoes a reaction which produces one or more ions 78, which diffuse to or flow over to the surface of the active sensor 72 where they interact with the active sensor 72 and cause a change in an electrical characteristic of the active sensor 72 and/or are detected by the active sensor 72.

The various devices described herein may utilize or work with a variety of functionalized structures and functionalized structure arrangements, as well as reactions between target chemical or biological substances and a functionalized structure and/or other reagents, to determine and/or detect various parameters of chemical or biological substances.

Figure 5:
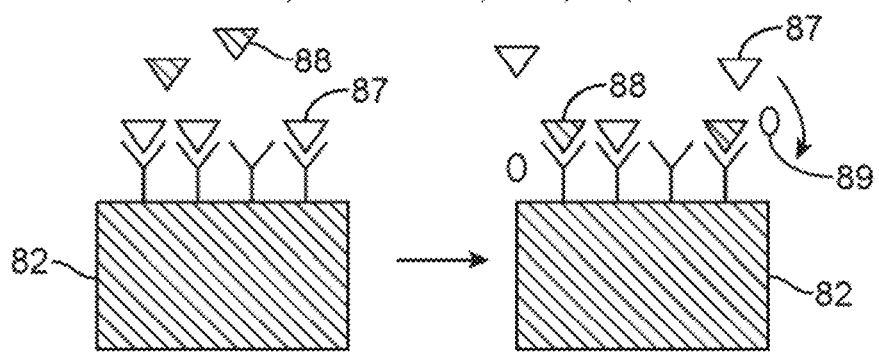
FIG. 5 illustrates a side view of an active sensor having functionalized structures disposed thereon, where first and second moieties of a chemical or biological substance undergo a competing reaction which produces ions which diffuse to the surface of the active sensor.

FIG. 5 illustrates a variation of an active sensor 82. Functionalized structures 85 are disposed on the surface of the active sensor 82. In this variation, a first moiety 87 and a second moiety 88 of a target chemical or biological substance undergo a competing reaction which produces ions 89, as the two moieties exchange binding position on the functionalized structure 85. The ions 89 then diffuse to the surface of the active sensor 82 where they interact with the active sensor 82 and cause a change in an electrical characteristic of the active sensor 82 and/or are detected by the active sensor 82.

Figure 6:
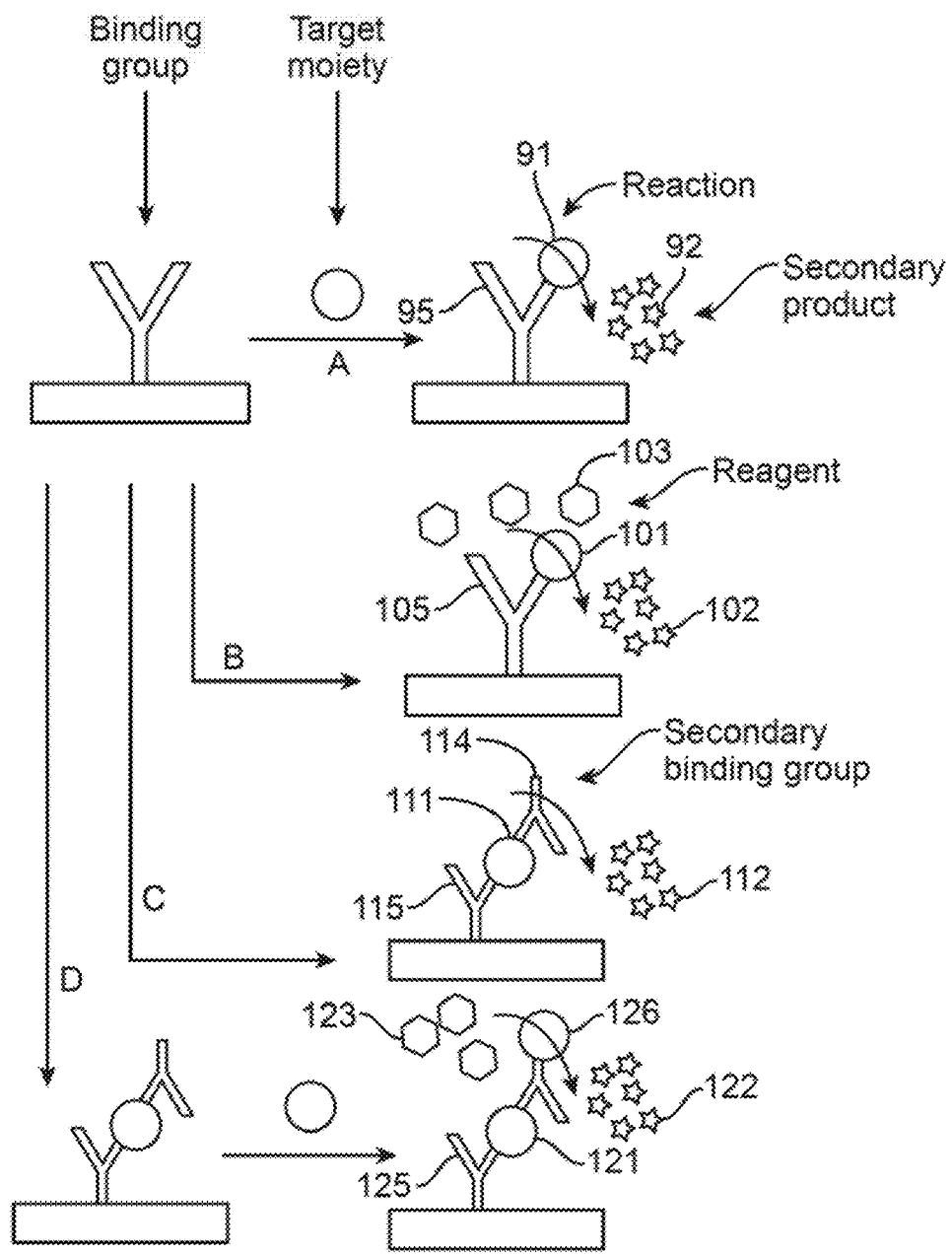
FIG. 6 illustrates various functionalization schemes and secondary reactions that a bound chemical or biological substance may undergo.

FIG. 6 illustrates various reactions that may be utilized with the sensor devices and systems described herein, which involve a chemical or biological substance binding to a functionalized structure disposed on a substrate, active sensor or in a location remote or separate from the sensor device or substrate. The reactions involve various functionalization schemes as described in more detail below.

In reaction A, a target moiety 91 binds functionalized structure 95, where the binding results in the production of a secondary product 92, which will effect a change in an electrical characteristic of an active sensor.

In reaction B, a target moiety 101 binds functionalized structure 105. The bound target moiety 101 undergoes a reaction with reagent 103, which results in the production of a secondary product 102, which will effect a change in an electrical characteristic of an active sensor.

In reaction C, a target moiety 111 binds functionalized structure 115. The bound target moiety 111 binds a secondary functionalized structure 114. The binding of the secondary functionalized structure 114 results in the production of a secondary product 112, which will effect a change in an electrical characteristic of an active sensor.

In reaction D, a first target moiety 121 binds functionalized structure 125. The bound first target moiety 121 binds a secondary functionalized structure 124. The secondary functionalized structure 124 binds a second target moiety 126. The bound second target moiety 126 undergoes a reaction with reagent 123, which results in the production of a secondary product 122, which will effect a change in an electrical characteristic of an active sensor.

In another example of a reaction, the reaction may include a species specific antibody (e.g. anti mouse, anti rabbit, anti goat, anti guinea pig, anti rat, anti lama), which is immobilized onto the sensor surface or other location separate from the sensor. Antigen-specific polyclonal and monoclonal primary antibodies raised in, e.g. mouse, rabbit, goat, guinea pig, rat or lama may be added and recognized by the secondary antibody immobilized to the sensor surface or other surface. For a stable interaction, chemical bifunctional cross linkers will be used to irreversibly connect both antibodies.

In other variations, peptides, oligos, ligands or other structures or molecules may be utilized to provide functionalization to a sensor or other surface. The functionalized structures may be involved or take part in various reactions, which can be detected or produce products that can be detected by the sensor.

In certain variations, the devices, systems and methods described herein may provide point-of-care, portable and real-time diagnostic tools. They may provide an electronic readout of an enzyme linked immunosorbent assay (ELISA) or other assays to detect various chemical or biological substances. The electronic components may be configured to transduce or convert a biochemical binding event or reaction into an electrical signal, which may be read out. Indirect detection of a freely diffusing, electronically active species produced at the site of a bound chemical or biological substance may be performed utilizing the described biosensor devices. Electronic readout ELISA schemes where an enzyme capable of producing an electronically active species may be utilized.

In one variation, indirect detection may be utilized in a device or system described herein where a surface is functionalized with binding receptors, such as capture antibodies or engineered proteins, in order to provide specific binding site. In one example, fms-like tyrosine kinase (sFlt1) may be detected. After sFlt1 is introduced to the device, it binds to the previously immobilized capture Abs. A secondary, biotin-labeled detection Ab is then introduced, which binds to a different epitope of sFlt1. Streptavidin (SA) conjugated GOx (SA-GOx) tagged enzyme is introduced to bind specifically to the detection Ab. Finally, glucose is introduced and the enzyme-mediated conversion of glucose to gluconic acid elicits a pH change that can be measured by the sensor.

FIG. 7 shows examples of reactions which cause secondary cascade reactions, which may be utilized with the devices described herein. The reactions listed in FIG. 7 are merely examples and not meant to be limiting, as other reactions my also cause secondary cascade reactions.

In certain variations, a functionalization area close to the sensor system or on the sensor surface where a functionalization and reaction take place is provided. The functionalization area may include an oxide surface, nanoparticles, a metal, polymer or any other kind of material. The functionalization can be a protein, antibody or a chemical moiety immobilized using a linker, which may consist of a chemical surface modification, immobilization linkers (such as Pro-Linker™) or anything else which allows to bind the functionalization moiety to the desired surface.

In certain variations, the functionalization can be in the form of an assay, e.g. sandwich assay. A reagent may be introduced to the sensor starting a cascade reaction creating the release of a moiety, e.g. ions. Secondary reagents may freely diffuse to the sensor surface or may be pushed to the surface using a force (e.g. pumps, capillary forces, etc).

In certain variations, a competing reaction may take place exchanging a previously captured moiety with another one, where the exchange of the moiety releases secondary ions.

In other variations, indirect detection of a freely diffusing, electronically active species produced at the site of a binding receptor-immobilized analyte can be performed. The reaction can create a change in the concentration of the released secondary ions. It may cause a change in pH (acid or base). Ions that can be released can be but are not limited to H+, Na+, K+, Cl−, COOH.

Functionalized Sensors Using Engineered Proteins.

Electrostatic- and charge-sensitive devices are often used in liquids as biochemical sensors. These sensors can directly transduce a biological binding event or biological reaction into an electronic signal in a label-free manner and are advantageous for sensor technologies demanding digital readout. Bio-detection in solution is inherently difficult due to the need of operating in buffered solutions with typically high ionic strength. Many times the ionic strength of a buffer has a strong influence on the sensitivity of the sensor as a result of its inverse square root relationship with the charge screening distance more commonly known as the Debye length: the higher the ionic concentration the lower is the screening length, which is available to detect the target.

Engineered proteins can provide a variety of advantageous features over other receptor molecules currently use for biomolecule detection. For example, Affimers™: a) small in size (~3 nm), b) highly stable (temperature, pH, proteolysis), c) highly selective, d) can be engineered in vitro to most target molecules including small molecules, and d) do not contain endogenous cysteines or functional groups apart from engineered ones that can be used for targeted surface immobilization.

When using electrostatic and charge-sensitive biochemical sensors a number of factors require consideration: i) specificity, ii) selectivity, iii) the distance of the binding receptor to the surface of the sensor (or target surface), and iv) uniform surface immobilization—meaning the binding receptor be placed uniformly. A number of binding groups and/or functional groups e.g., e.g. antibodies, aptamers, DNA, etc. can sufficiently address specificity and selectivity. However, the distance of the binding receptor the target surface and uniform surface immobilization are not well addressed by many binding groups. Such considerations render many FET based sensors using conventional binding receptors molecules with an inability to measure detection events in high ionic strength buffers.

For example, the distance of the binding receptor's binding site to the target surface is limited by the actual size of the binding receptor. Antibodies for instance are ~15 nm in size and require buffered solutions at high ion concentrations of ~150 mM for proper performance. However, operating the sensor at these parameters, the charge screening length is reduced to a few nm such that the sensor will not sense most of the binding reactions and signals. Moreover, for most binding receptors, including antibodies, an adhesion layer is required for surface immobilization thereby increasing the distance to the target surface even more.

The use of small receptors, such as engineered proteins (e.g., 3 nm in size), can overcome the inability to measure detection events in high ionic strength buffers. This permits improved performance since biomolecules and their biochemical reactions can occur at ionic strengths that mimic physiological environments. The use of a binding receptor that is closer to the sensor interface dramatically helps overcome many conventional screening limitations. In addition a more stable binding receptor allows use of the FET sensor in different surrounding conditions, such as temperature, lower ionic or variable pH solutions and thereby facilitates sample preparation and increases the storage capacity and shelf life of the functionalized sensor.

Figure 8A:
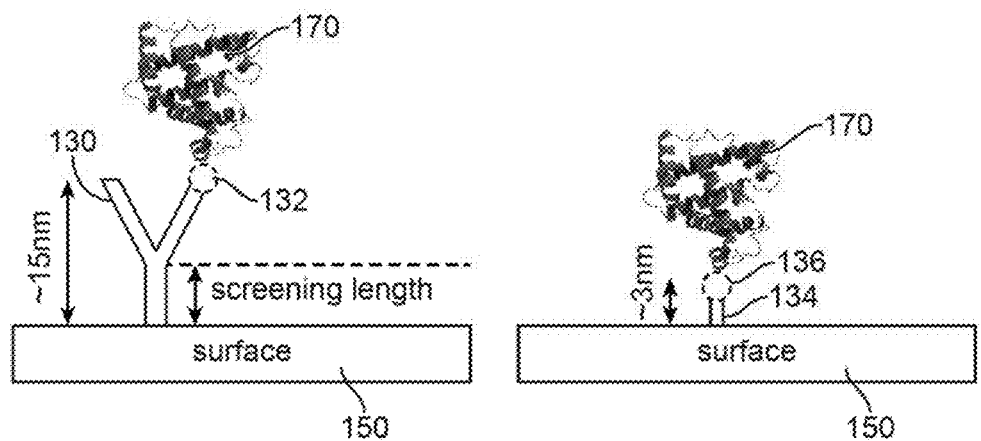
FIG. 8A provides an illustrative example of the differences between a binding site of conventional receptor molecule and binding receptors with a minimized binding site length, which lies within the or in close proximity to the screening length instead of outside.

FIG. 8A illustrates an example of a conventional receptor molecule 130 currently use for biomolecule detection. As shown, the screening distance or target binding site 132 of a conventional receptor molecule 130 can be 15 nm from the immobilization surface of the sensor 150 and thus outside the screening distance. Reducing the distance of the binding site, for example, using the engineered protein 134 reduces the binding distance of the target binding site 136 to approximately around 3 nm or less. Typically, the screening length is depended on the background ion concentration where reducing the ion concentration can increase the screening length. In any case, the greater the distance of the binding site from the surface, the lower the probability of detection of a binding event. Therefore, reducing the distance of the binding site increases the probability that a binding event will even be sensed/detected by the sensor and is especially useful where solutions of high ion concentrations are desired. As noted above, many conventional receptor molecules also require an adhesion layer to immobilize the receptor molecule onto the surface of the sensor. Such an additional layer further increases the binding distance between the binding site and the surface of the sensor 150. In contrast, the use of an engineered protein 134 eliminates the need for such an adhesion layer.

Moreover, use of a binding receptor that is free of endogenous functional groups improves uniform surface immobilization—meaning the binding receptor can be placed uniformly. In many cases, use of a binding receptor that has one or more targeted surface functional groups engineered directly onto the binding receptor further decreases the distance to the sensor interface and also allows for a highly uniform surface.

Figure 8B:
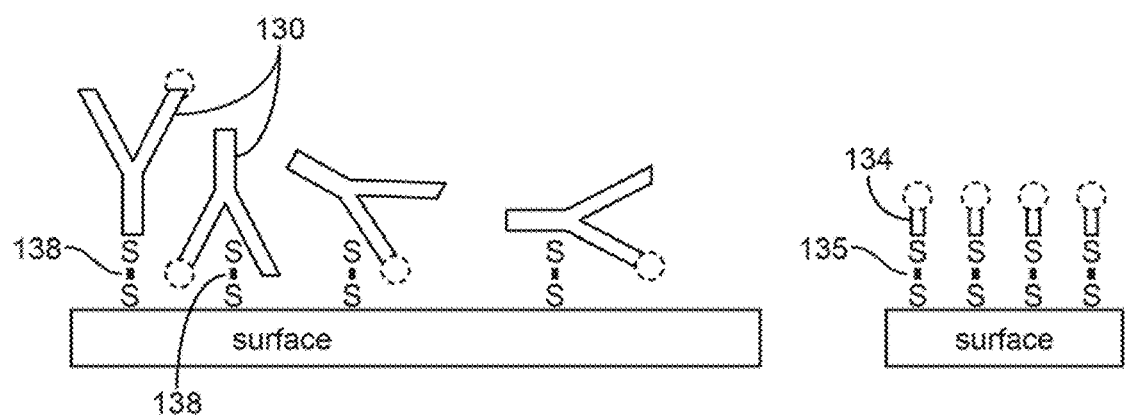
FIG. 8B provides an example of an endogenous functionalized group on a conventional receptor molecule and a binding receptors with an engineered functionalized group that immobilizes the binding receptor to the sensor.

For example, FIG. 8B illustrates a conventional receptor molecule 130 as having one or more endogenous functional groups 138 (e.g., cysteines) throughout the molecule 130. The presence of these endogenous functional groups 138 introduces variability in the location of the adhesion site relative to the surface of the sensor. In certain cases, an additional adhesion layer is required to improve uniformity. In contrast, the engineered protein 134 depicted in FIG. 8B can include a targeted functionalization group 135 to functionalize (or immobilize) the engineered protein 134 onto the desired surface of the sensor in a consistent or desired manner. Although the targeted functional group 135 of the engineered protein 134 is depicted to be located on an end of the structure 134, one or more functionalization groups can be positioned as desired on any respective part of the protein structure 134.

In one example electrostatic- and charge-sensitive devices used in a liquid as biochemical sensor can be covered with a thin metal layer, such as gold or other metal that is resistant to corrosion and oxidation in moist air (e.g., a noble metal). In another variation, the same sensor can be covered with nanoparticles, including but not limited to metal nanoparticles, semiconductor layers, an insulator material, or a magnetic material. Further any other shape of a material can be used to cover the sensor. The improved binding receptor (e.g., the engineered protein) is then directly attached to the metal layer or nanoparticle using any conventional process (e.g. thiol chemistry to bind to gold or other metal). In additional variations the sensor does not require any metal layer. Instead, the sensor can be functionalized on any number of surfaces on the sensor or next to the sensor (e.g. oxide surface or any other type of surface).

Figure 9:
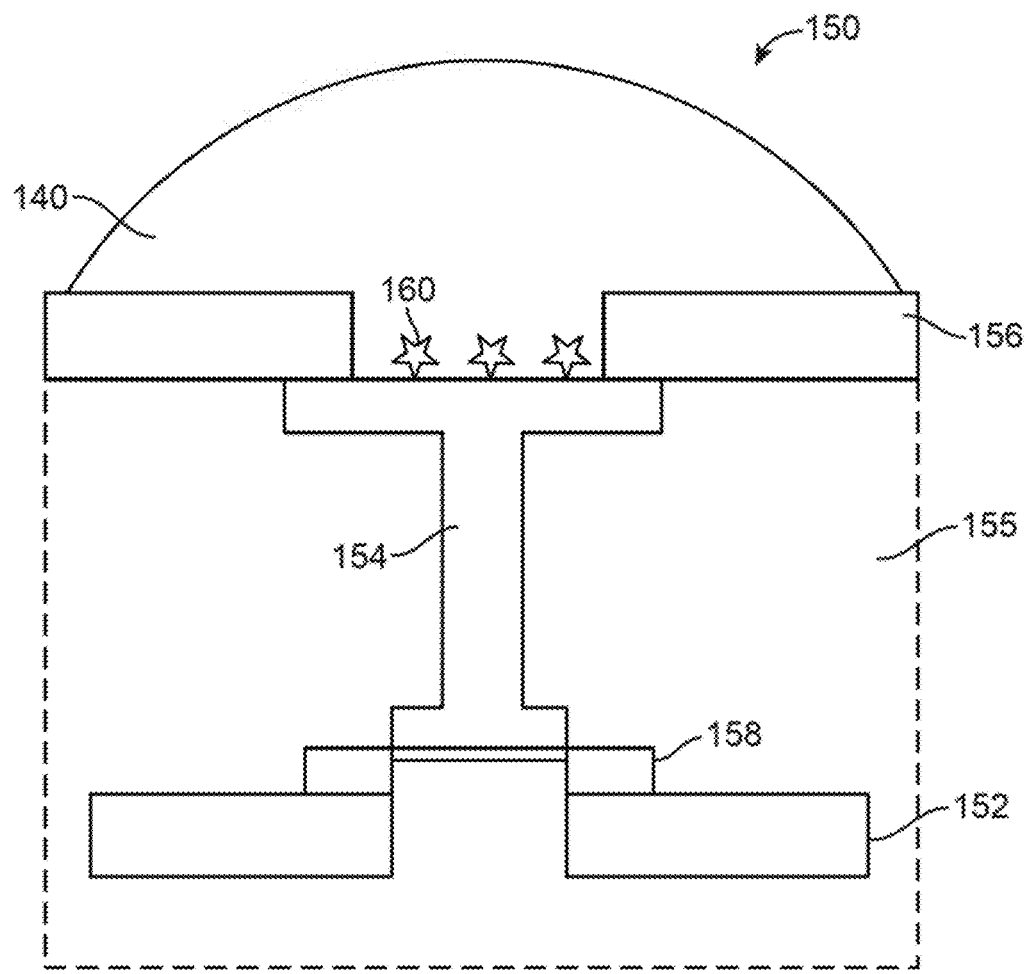
FIG. 9 shows one example of a FET sensor used to determine a parameter of a substance in a test sample.

FIG. 9 shows one example of a FET sensor 150 used to determine a parameter of a substance in a test sample 140 (typically a liquid). The charge sensitive or electrostatic device 152 can be covered with a layer such as nanoparticles as described above, or a metal, to form an extended gate 154. The extended gate (e.g., the metal or nanoparticle layer) 154 is then covered with an encapsulation layer 156 that expose a portion of the extended gate 154. The encapsulation layer 156 serves to protect the device from being exposed to environment factors that would damage or degrade the sensor (e.g, such as excess fluids or leakage currents). In certain variations, the encapsulation layer 156 covers the whole sensor chip/strip with an only opening for the extended gate area or other geometry opening over the sensor area.

The encapsulation layer can be any material that is unaffected or less affected by the environment of the test sample or by general conditions prior to use of the FET sensor 150. The improved binding receptor (such as the engineered protein) 160 is then directly attached to the extended gate layer 154 using any known technique (e.g., in cases of a gold gate layer, thiol chemistry can bind the binding receptor 160 to the extended gate 154). The sensor can also include a non-conductive material 155, including but not limited to a polymer, dielectric, oxide, nitride, etc. As shown, the exposed gate 154 is in contact with the test sample 140 that is functionalized with the engineered protein 160 as described above.

Figure 10A:
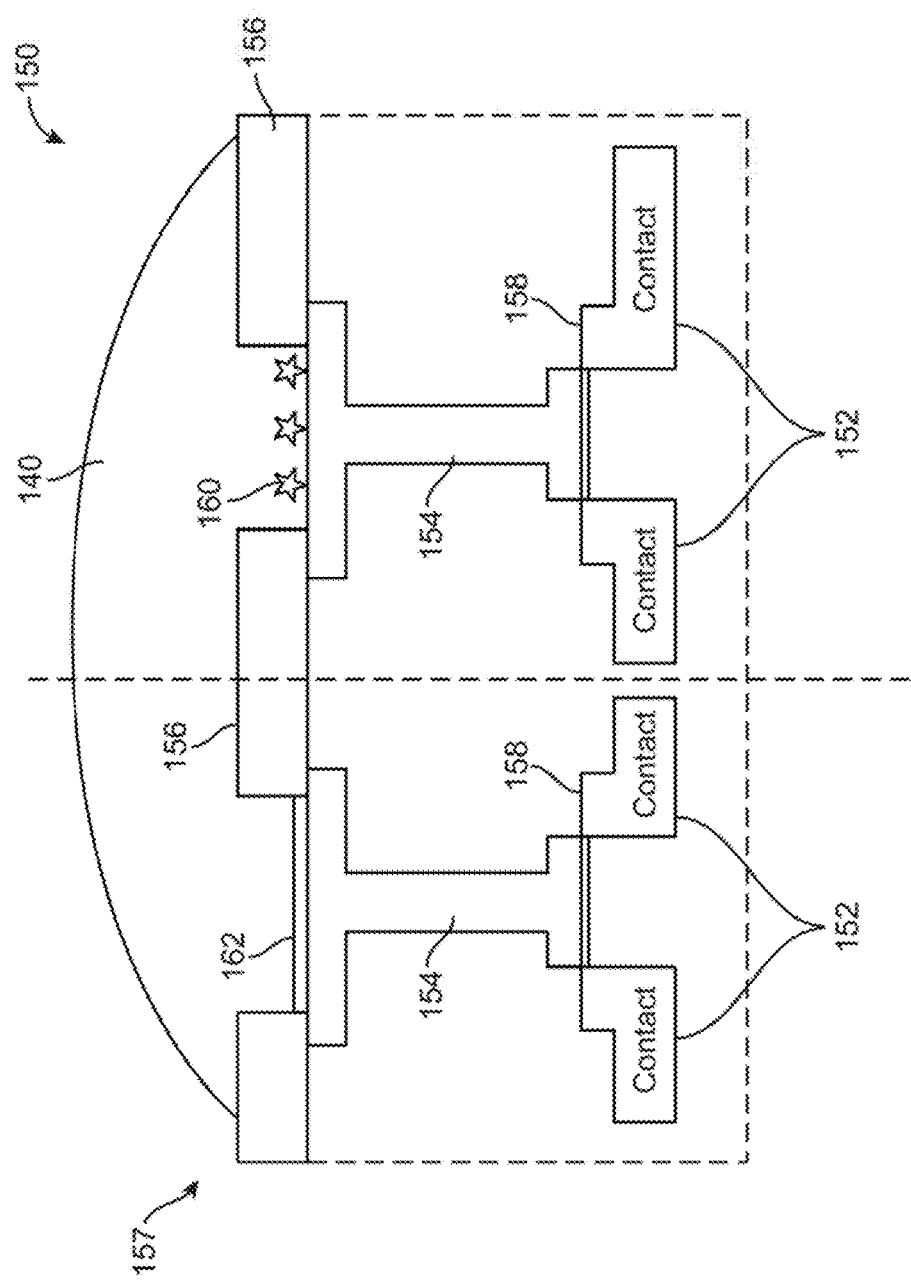
FIG. 10A illustrates an example of a device that increases the reliability of measurement of a substance in the test sample using a signal comparison between two sensors.

FIG. 10A illustrates another example that increases the reliability of measurement of a substance in the test sample 140 using an assessment and/or comparison of signals between two sensors. For example, the two sensors 150, 151 can both be covered with an encapsulation layer such the described metal or nanoparticle layer 154 where only one sensor 150 is functionalized with the engineered protein 160 while the other sensor 151 is either passivated (with a passivation layer) or is simply not functionalized with any binding receptor 160. In the illustrated example, the second reference sensor 151 can optionally include a second passivation layer 162 that makes the sensor 151 just inherent or prevents a reaction with the target moiety. In the illustrated examples, the sensor 150 includes an extended gate 154 having a surface that is functionalized with the binding receptor 160, where the functionalized surface interacts with the sample 140.

As described above, the functionalized sensor 150 is functionalized with binding receptors (e.g., the engineered protein) that have at least one functional group associated therewith such that the functional group on each of the binding receptors permits securing each of the binding receptors to a first layer of the sensor (in this case an extended gate 154) in a desired manner (e.g., the functional groups can secure the binding receptors in a uniform manner). When placed in contact with the test sample, the binding receptor interacts with the substance in the test sample such that interaction of the substance with the functionalized sensor results in a change in the electrical characteristic of the sensor (in this example the electrical characteristic is affected by the change of the extended gate across the sensor channel 158 or in its vicinity). This change causes the sensor 152 to produce a changed electrical characteristic that can be detected upon the application of an electrical stimulus. Such a stimulus can include, but is not limited to application of a voltage, current, frequency or other signal allowing detection of the changed electrical characteristic from the native electrical characteristic of the sensor. Comparison of the changed electrical characteristic against the native electrical characteristic or the control sensor allows determining the parameter of the substance within the test sample.

Figure 10B:
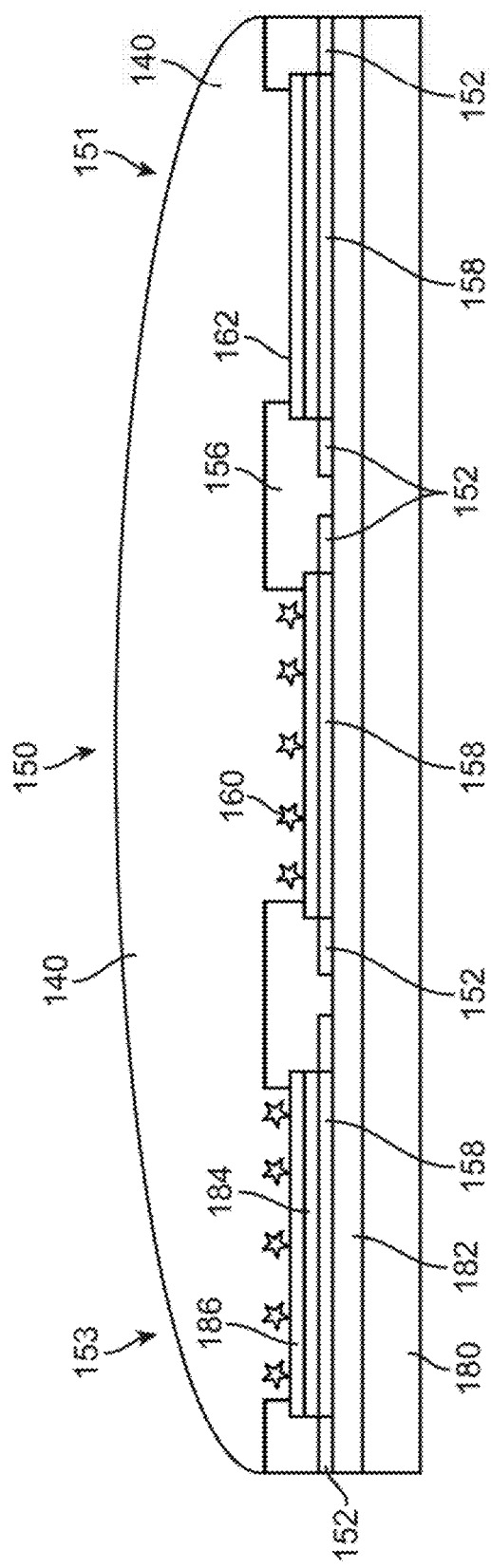
FIG. 10B illustrates additional variations of functionalized sensors and a reference sensor.

FIG. 10B illustrates additional variations of structures for determining a parameter of a substance in a test substance, the device comprising two functionalized sensors 150, 153 and a control sensor. 151. The illustrations are intended to show various configurations of the sensors. As illustrated, the sensors can be placed on substrate layer 180 that can comprise any material such as an oxide layer or a polymer layer. In one example, the substrate 180 comprises silicon or a similar material that allows a voltage to be applied through the substrate layer 180 as opposed to the liquid sample 140. Next a dielectric layer 182 (such as an oxide material) is applied to permit electrical isolation of the various sensors.

The sensor contacts 152 are located on the dielectric layer 182 and are bridged with a sensor channel 158. The sensor channel 158 can comprise any electrically conductive material, structure, layer or coating that allows for electrical communication between the sensor contacts 152. Next, a high-k dielectric material 184 (including but not limited to aluminum oxide, titanium oxide, zirconium oxide, yttrium oxide, silicon oxide, tantalum oxide, hafnium oxide and silicon nitride) is deposited over the gate and/or sensor contacts to permit immobilization of the functionalization layer or binding receptors and to reduce potential leakage currents (as shown in sensor 150).

As noted above, variations of the device (e.g., sensor 153) can include a high-k dielectric layer 184 with an additional metal and/or nanoparticle layer 186 disposed on the high-k dielectric layer 184 and a functionalization layer 160 immobilized on the metal/nanoparticle layer 186. Alternatively, the layer 182 can be completely removed.

Reference sensor 151 of FIG. 9B illustrates a passivation layer 162 located on a high-k dielectric layer 184. However, in additional variations, the reference sensor can include a metal/nanopartical layer 186 with or without a passivation layer 162. In either case, the reference sensor will not include a functionalization layer.

As noted above, the test sample can comprise a bodily fluid, or any other fluid that contains a substance that can be detected upon binding to the binding receptor.

For example, engineered proteins can be used in conjunction with the active or functionalized sensor 150 to detect biological and chemical molecules from human or other animal bodily fluids, including but not limited to urine, blood, saliva, tears, ejaculate.

Engineered proteins can be engineered with targeted terminal or internal functional groups such as cysteines and immobilized onto a surface (e.g., gold or other noble metal) or suitable nano particles of the active sensor (or an extension of the active sensor such as an extended gate) using any known process for immobilization.

In another variation, the engineered proteins can be engineered with N- or C-terminal or internal cysteines and immobilized onto the active sensor surface/nanoparticles modified by self-assembled monolayers (SAMs) using thiol (—SH) chemistry.

Engineered proteins can be immobilized onto the active sensor surface/nanoparticles coated with carboxylic acid-SAM and using amide coupling. Alternatively, any other type of SAM layer can be used.

The functionalized sensors can use engineered proteins engineered with terminal streptavidin and immobilized onto (solid supports and) the active sensor surface/nanoparticles coated with self biotin-SAMs.

Engineered proteins can be engineered with terminal histidine tags and immobilized on (solid supports and) the active sensor gold surface/gold nanoparticles coated with a $Ni^{2+}$–NTA (nitrilotriacetic acid) chelating moiety. In another application the proteins can be engineered as biotin fusion proteins and immobilized onto streptavidin functionalized surfaces (or visa versa). Any number of tags can be engineered depending upon the desired application.

Immobilization of the engineered proteins can occur via an $NH_2$-functionality onto the $SiO_2$ surface of the active sensor by silane chemistry. In another application, modification of the charge of $SiO_2$ can be made by application of short amphiphylic synthetic peptides.

In an additional variation, engineered proteins are generated or used as specific ligands for bacterial endo- and exotoxins. In another application, endo- and exotoxin binding (analyte binding) to the engineered protein happens directly on the sensor surface biofunctionalized and activated with the engineered capture proteins.

Figure 11A:
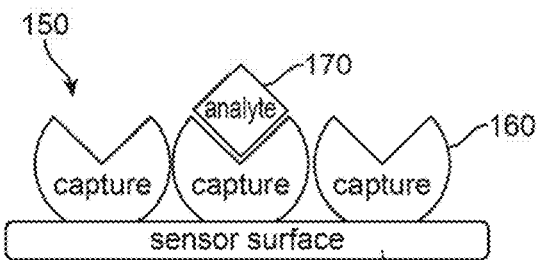
FIGS. 11A to 11C provide illustrations of various binding receptors and secondary reactions that can be measured by the sensor.
Figure 11B:
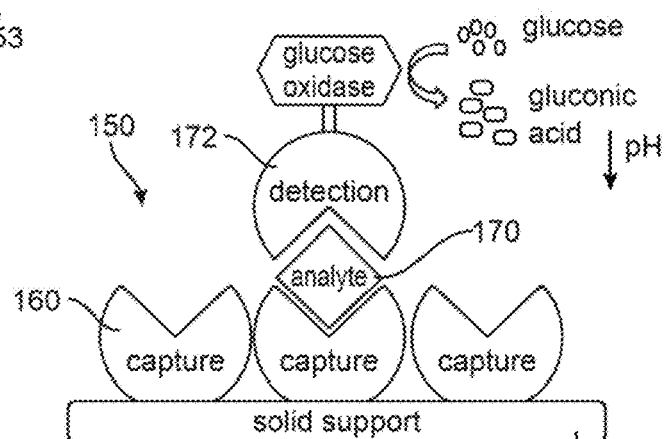
Figure 11C:
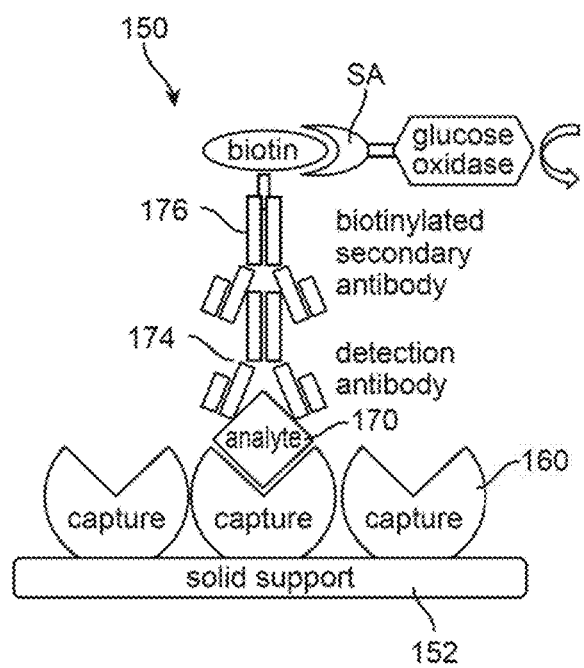

For example FIGS. 11A to 11C provide illustrations of a binding receptor, such as the engineered protein, functionalized on the sensor 152 (or on the extended gate, not shown).

FIG. 11A shows an analyte 170 (e.g., a substance contained in the test sample) binding to a binding receptor 160 that is immobilized on a surface of an active sensor 153 to produce a change in the electrical characteristics electrical component of the sensor.

FIG. 11B illustrates a variation of a functionalized sensor 150 where the binding receptor 160 is immobilized on a layer of the sensor 153 (e.g., the gate, metal layer, and/or high-k dielectric as described above) that allows binding of the analyte 170. However, in this variation, a second binding receptor 172 (such as a glucose oxidase tethered to the engineered protein) is introduced to the sensor and binds to a different analyte 170 binding site. Next, a substance can be added to enzymatically cause the second binding receptor 172 to generate a reaction that can be measured by the active sensor 153. In the present example, the addition of glucose can cause a reaction that generates gluconic acid and elicits a pH change that can be measured by the active sensor.

FIG. 11C shows another variation or application where endo- and exotoxin binding to the binding receptor 160 occurs indirectly on a sensor biofunctionalized with the binding receptor separate from the active sensor 153. As shown, binding receptors 160 immobilized on the sensor 153 to bind their target analyte 160. Next, a detection antibody 174 is introduced that binds to a different site of the analyte molecule 170. Then, a secondary, biotin labeled antibody 176 can be added that recognizes and binds to the primary detection antibody 174. Next, a streptavidin (SA)-bound glucose oxidase is introduced to bind biotin tethered to the secondary antibody 176. This converts glucose to gluconic acid, eliciting a pH change that can be measured by the active sensor in a second location.

In another variation, an actual target molecule (i.e., the substance to be detected by sensor) can be immobilized on the sensor or substrate surface and the binding receptor (e.g. an engineered protein or engineered scaffold protein, an antibody, peptide etc.) is applied to bind the target molecule. When the actual substance in a test sample is applied to the sensor, the substance in the test sample competes for the bound engineered protein, thereby releasing the bound receptor and producing a change in the electric signal of the sensor as noted above.

The binding receptors can be generated or used as specific ligand for a number of applications, including but not limited to disease causing microorganisms including bacteria, yeast, fungi, viruses, parasites; for yeast biomarker, fungal biomarker, viral proteins; a specific ligand for tumor cells or other cells; as specific ligands for disease-related and drug-related biomarkers (proteins, antibodies, peptides, polysaccharides, lipids, hormones); as specific ligand for small molecules (drugs, therapeutics) or drugs subject to abuse; as specific ligand for nucleic acids; as specific ligand for heavy metal ions; and as specific ligand for multi-drug resistance proteins causing resistance to distinct antimicrobials, antibiotics, antifungal drugs, antiviral medications, antiparasitic drugs, chemicals of a wide variety of structure and function targeted at eradicating the organism.

Any of the functionalization schemes and reactions described herein may take place in a first location remote from or separated from the sensor or device located in a second location. The reaction products or ions may then flow to and/or over the sensor or device where detection takes place.

Each of the individual variations described and illustrated herein has discrete components and features which may be readily separated from or combined with the features of any of the other variations. Modifications may be made to adapt a particular situation, material, composition of matter, process, process act(s) or step(s) to the objective(s), spirit or scope of the present invention.

Methods recited herein may be carried out in any order of the recited events which is logically possible, as well as the recited order of events. Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

What is claimed is:

1. A device for determining a parameter of a substance in a sample, the device comprising:
    a substrate having an active sensor disposed above the substrate, wherein the active sensor responds to an electrostatic or capacitance change;
    wherein the active sensor comprises a metal layer and a first electrical component having an electrical characteristic;
    a functionalized structure comprising a plurality of binding receptors each having at least one cysteine group directly engineered on each of the binding receptors such that the cysteine group on each of the binding receptors secures each of the binding receptors directly to the metal layer of the active sensor and the distance between each of the binding receptors and the metal layer is 5 nm or less, wherein the plurality of binding receptors are configured to bind with the substance to undergo a reaction resulting in the release of ions such that the release of the ions results in a change in the electrical characteristic of the first electrical component independent of current flow in solution; and wherein the first electrical component is configured to generate a signal upon the application of an electrical stimulus, the signal being indicative of the changed electrical characteristic of the first electrical component and wherein the parameter of the substance is determined by the signal indicative of the changed electrical characteristic of the first electrical component.

2. The device of claim 1, wherein the electrical stimulus comprises altering an electrical parameter selected from the group consisting of frequency, current, voltage, resistance, inmpedance, capacitance, conductivity, induction, threshold voltage, transconductance, subthreshold swing, piezo-resistivity, magnetic field, and electrical noise.

3. The device of claim 1, wherein each of the binding receptors comprises a protein.

4. The device of claim 1, wherein the cysteine group is directly engineered on each of the binding receptors in a targeted fashion.

5. The device of claim 1, wherein the plurality of binding receptors are positioned uniformly on the active sensor to bind the substance, wherein binding of the substance with the functionalized structure changes the electrical characteristic of the first electrical component.

6. The device of claim 1, wherein the determined parameter of the substance in the sample is concentration.

7. The device of claim 1, wherein the substance includes, a therapeutic, drug, biological moiety, chemical moiety, protein, toxin, ion, antibody, peptide, oligonucleotide, pathogen, cells, or small molecules.

8. The device of claim 1, wherein the first electrical component is selected from the group consisting of a transistor, a capacitor, a resistor and an inverter.

9. The device of claim 1, wherein the cysteine group on each of the binding receptors secures each of the binding receptors directly to the metal layer of the active sensor without an intervening molecule or without a self-assembled monolayer in between the cysteine group and the metal layer.

10. The device of claim 1, wherein the metal layer is a gold layer.

11. A device for determining a parameter of a substance in a sample, the device comprising:
a substrate having an active sensor and a control sensor, wherein the active sensor is disposed above the substrate and responds to an electrostatic or capacitance change;
wherein the active sensor comprises a metal layer and a first electrical component having a first electrical characteristic and the control sensor comprises a second electrical component having a second electrical characteristic;
a functionalized structure comprising a plurality of binding receptors each having at least one cysteine group directly engineered on each of the binding receptors such that the cysteine group on each of the binding receptors secures each of the binding receptors directly to the metal layer of the active sensor and the distance between each of the binding receptors and the metal layer is 5 nm or less, wherein the plurality of binding receptors are configured to bind with the substance to undergo a reaction resulting in the release of ions such that the release of the ions results in a change in the first electrical characteristic of the first electrical component independent of current flow in solution;

wherein the first electrical component is configured to generate a first signal upon the application of an electrical stimulus and the second electrical component is configured to generate a second signal upon the application of the electrical stimulus; and wherein the parameter of the substance is determined by a difference between the first signal and the second signal.

12. The device of claim 11, wherein the electrical stimulus comprises altering an electrical parameter selected from the group consisting of frequency, current, voltage, resistance, impedance, capacitance, conductivity, induction, threshold voltage, transconductance, subthreshold swing, piezo-resistivity, magnetic field, and electrical noise.

13. The device of claim 11, wherein the plurality of binding receptors are positioned uniformly on the active sensor to bind the substance, wherein binding of the substance with the functionalized structure changes the first electrical characteristic of the first electrical component.

14. The device of claim 11, wherein the substance includes, a therapeutic, drug, biological moiety, chemical moiety, protein, toxin, ion, antibody, peptide, oligonucleotide, pathogen, cells, or small molecules.

15. The device of claim 11, wherein at least one of the first electrical component and the second electrical component is selected from the group consisting of a transistor, a capacitor, a resistor and an inverter.

16. The device of claim 11, wherein the control sensor comprises a passivation layer.

17. The device of claim 11, wherein the cysteine group on each of the binding receptors secures each of the binding receptors directly to the metal layer of the active sensor without an intervening molecule or without a self-assembled monolayer in between the cysteine group and the metal layer.

18. The device of claim 11, wherein the metal layer is a gold layer.

19. A device for determining a parameter of a substance in a sample, the device comprising:
a substrate having an active sensor disposed above the substrate and responds to an electrostatic or capacitance change;
wherein the active sensor comprises a metal layer and a first electrical component having a first electrical characteristic:
a functionalized structure comprising a plurality of binding receptors each having at least one cysteine group directly engineered on each of the binding receptors such that the cysteine group on each of the binding receptors secures each of the binding receptors directly to the metal layer of the active sensor and the distance between each of the binding receptors and the metal layer is 5 nm or less, wherein the plurality of binding receptors are configured to bind with the substance;
a plurality of first molecules in a vicinity of the active sensor, wherein each of the plurality of first molecules comprises a plurality of second binding receptors, and wherein at least one of the plurality of second binding receptors is bound to a different site of the substance bound by at least one of the plurality of binding receptors;
a plurality of second molecules in the vicinity of the active sensor, wherein the plurality of second molecules reacts with the plurality of first molecules through an enzymatic reaction to release ions in the vicinity of the active sensor such that the release of the ions results in the change in the electrical characteristic of the first electrical component independent of current flow in solution;

wherein the first electrical component is configured to generate a signal upon the application of an electrical stimulus and wherein the signal is indicative of the changed electrical characteristic of the first electrical component; and wherein the parameter of the substance is determined by the signal indicative of the changed electrical characteristic of the first electrical component.

20. A device for determining a parameter of a substance in a sample, the device comprising:

a substrate having an active sensor and a control sensor, wherein the active sensor is disposed above the substrate and responds to an electrostatic or capacitance change;

wherein the active sensor comprises a metal layer and a first electrical component having a first electrical characteristic and the control sensor comprises a second electrical component having a second electrical characteristic;

a functionalized structure comprising a plurality of binding receptors each having at least one cysteine group directly engineered on each of the binding receptors such that the cysteine group on each of the binding receptors secures each of the binding receptors directly to the metal layer of the active sensor and the distance between each of the binding receptors and the metal layer is 5 nm or less, wherein the plurality of binding receptors are configured to bind with the substance;

a plurality of first molecules in a vicinity of the active sensor, wherein each of the plurality of first molecules comprises a plurality of second binding receptors, and wherein at least one of the plurality of second binding receptors is bound to a different site of the substance bound by at least one of the plurality of binding receptors;

a plurality of second molecules in the vicinity of the active sensor, wherein the plurality of second molecules reacts with the plurality of first molecules through an enzymatic reaction to release ions in the vicinity of the active sensor such that the release of the ions results in the change in the electrical characteristic of the first electrical component independent of current flow in solution;

wherein the first electrical component is configured to generate a first signal upon the application of an electrical stimulus and the second electrical component is configured to generate a second signal upon the application of the electrical stimulus; and wherein the parameter of the substance is determined by a difference between the first signal and the second signal.

* * * * *